(12) United States Patent
Boitor et al.

(10) Patent No.: US 8,535,300 B2
(45) Date of Patent: Sep. 17, 2013

(54) SURGICAL LASER TIP APPARATUS WITH ALIGNMENT ASSEMBLY

(75) Inventors: Mihai I. A. Boitor, Martinez, CA (US); Alexandre B. Di Sessa, Walnut Creek, CA (US)

(73) Assignee: Zila, Inc., Fort Collins, CO (US)

( * ) Notice: Subject to any disclaimer, the term of this patent is extended or adjusted under 35 U.S.C. 154(b) by 1309 days.

(21) Appl. No.: 12/257,665

(22) Filed: Oct. 24, 2008

(65) Prior Publication Data
US 2010/0106147 A1   Apr. 29, 2010

(51) Int. Cl.
*A61B 18/22*   (2006.01)

(52) U.S. Cl.
USPC .......................................................... 606/16

(58) Field of Classification Search
USPC ................................................ 606/1, 13, 16
See application file for complete search history.

(56) References Cited

U.S. PATENT DOCUMENTS

| | | | |
|---|---|---|---|
| 4,580,557 A | 4/1986 | Hertzmann | |
| 4,919,508 A | 4/1990 | Grace | |
| 5,304,172 A | 4/1994 | Manoukian et al. | |
| 5,464,436 A | 11/1995 | Smith | |
| 5,551,448 A | 9/1996 | Matula et al. | |
| 5,607,420 A | 3/1997 | Schuman | |
| 5,616,141 A | 4/1997 | Cipolla | |
| 5,927,977 A | 7/1999 | Sale et al. | |
| 5,928,220 A | 7/1999 | Shimoji | |
| 6,013,096 A | 1/2000 | Tucek | |
| 6,039,565 A | 3/2000 | Chou et al. | |
| 6,099,520 A | 8/2000 | Shimoji | |
| 6,213,998 B1 | 4/2001 | Shen et al. | |
| 6,231,567 B1 | 5/2001 | Rizoiu et al. | |
| 6,254,597 B1 | 7/2001 | Rizoiu et al. | |
| 6,261,310 B1 | 7/2001 | Neuberger et al. | |
| 6,325,791 B1 | 12/2001 | Shimoji | |
| 6,327,942 B1 | 12/2001 | Mariol et al. | |
| 6,458,120 B1 | 10/2002 | Shen et al. | |
| 6,572,637 B1 | 6/2003 | Yamazaki et al. | |
| 6,574,401 B2 | 6/2003 | Neuberger et al. | |
| 6,746,473 B2 | 6/2004 | Shanks et al. | |
| D496,101 S | 9/2004 | Davison | |
| 6,868,221 B1 | 3/2005 | Wood et al. | |
| 7,033,350 B2 | 4/2006 | Bahk | |
| 7,118,563 B2 | 10/2006 | Weckwerth et al. | |
| 7,137,977 B2 | 11/2006 | Brucker et al. | |
| 7,267,672 B2 | 9/2007 | Altshuler et al. | |
| 7,288,086 B1 | 10/2007 | Andriasyan | |
| 7,290,940 B2 | 11/2007 | Boutoussov | |
| 7,320,594 B1 | 1/2008 | Rizoiu et al. | |
| 8,277,442 B2 * | 10/2012 | Di Sessa et al. | 606/1 |
| 2001/0007347 A1 | 7/2001 | Shimada et al. | |
| 2004/0259053 A1 | 12/2004 | Bekov et al. | |
| 2006/0064080 A1 | 3/2006 | Cao | |
| 2007/0055291 A1 | 3/2007 | Birkmeyer et al. | |

FOREIGN PATENT DOCUMENTS

| | | |
|---|---|---|
| EP | 0408160 A1 | 1/1991 |
| EP | 0473987 A1 | 3/1992 |
| EP | 0951921 A2 | 10/1999 |
| WO | WO 01/10327 A1 | 2/2001 |
| WO | 0198054 A1 | 12/2001 |
| WO | 0235264 A1 | 5/2002 |
| WO | 2008092042 A2 | 7/2008 |

OTHER PUBLICATIONS

Extended European search report dated Jun. 15, 2012, issued by European Patent Office in related EP Application No. 09 822 419.9.
Office Action issued on Jan. 4, 2013, in related Chinese Patent Application 200980141923.6.

* cited by examiner

*Primary Examiner* — Samantha Shterengarts
(74) *Attorney, Agent, or Firm* — Jeffer Mangels Butler & Mitchell LLP

(57) ABSTRACT

An assembly for alignment of a sterile, releasably locking optical tip assembly housing an optical fiber connection to a laser surgical device includes a conductive wire sensing element. A second embodiment includes an emitter and a detector.

7 Claims, 2 Drawing Sheets

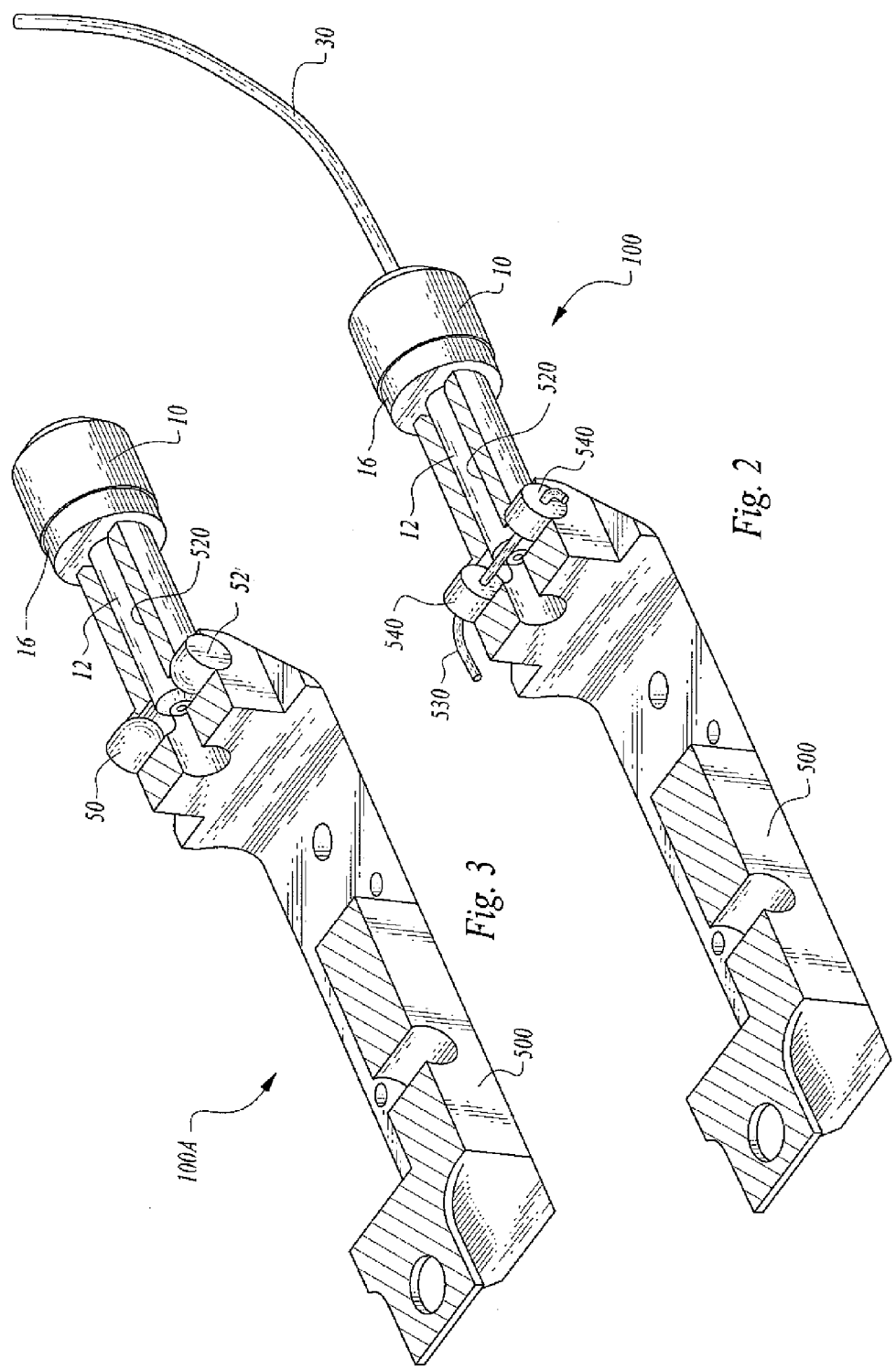

SURGICAL LASER TIP APPARATUS WITH ALIGNMENT ASSEMBLY

CROSS-REFERENCES TO RELATED APPLICATIONS

None.

STATEMENT REGARDING FEDERALLY SPONSORED RESEARCH OR DEVELOPMENT

None.

REFERENCE TO A MICRO-FICHE APPENDIX

None.

BACKGROUND OF THE INVENTION

This invention relates to surgical instruments for laser ablation procedures. More particularly, the invention relates to a tip apparatus having an assembly for proper optical fiber alignment with a laser diode for such surgical instruments.

BRIEF SUMMARY OF THE INVENTION

In practice, medical laser treatment using hand-held instruments has generally been developed for ophthalmic, dental, orthopedic, and similar surgical procedures where the treatment area is confined or particularly difficult to reach. Typically, laser light is transmitted from a laser source though an optical fiber to a treatment site. The optical fiber terminates proximally in a laser source connector for connection to the laser source and terminates distally in a handpiece manipulated by the surgeon.

With known systems, a handpiece used during one procedure often cannot be used with another patient in a subsequent procedure unless some form of sterilization is performed. Types of sterilization techniques range from autoclaves to gas. Gas procedures are time consuming and costly. Autoclave temperatures generally have proven too severe for laser surgical handpieces to withstand. These problems could be overcome using a sterile, disposable tip for use with a laser surgical device. Use of disposable tips, however, present optical alignment problems between the tips and the diode laser source in the surgical instrument.

Accordingly it would be useful to provide a sterile, disposable tip having a quick and easy to use alignment and connection assembly for use with a laser surgical device, such as our disposable surgical tip apparatus disclosed and claimed in pending U.S. Non-provisional patent application Ser. No. 12/115,336, filed on May 5, 2008 ["the '336 Application"] which is incorporated herein by reference for all purposes.

It would be of further use if the sterile, disposable tip provided means for precise alignment of the optical fiber in the tip to the source of laser energy in the surgical device.

Yet another useful advantage would be for the sterile, disposable tip to be releasably attached to the device with precise optical, mechanical, magnetic, electro-mechanical, or electromagnetic locking and alignment assembly.

For a more complete understanding of the above and other features, advantages, and objects of the invention, reference should be made to the following detailed description of a preferred embodiment, and to the accompanying drawings.

BRIEF DESCRIPTION OF DRAWINGS

FIG. 2 is a cut away perspective view of a first embodiment of an assembled reusable surgical device laser housing 500 of FIG. 1 taken at "2-2" with the disposable tip apparatus 100 adapted thereto.

FIG. 3 is a cut away perspective view of a second embodiment of an assembled reusable surgical device laser housing 500 with the disposable tip apparatus 100A with alignment assembly adapted thereto.

DETAILED DESCRIPTION OF THE INVENTION

Figure 1:
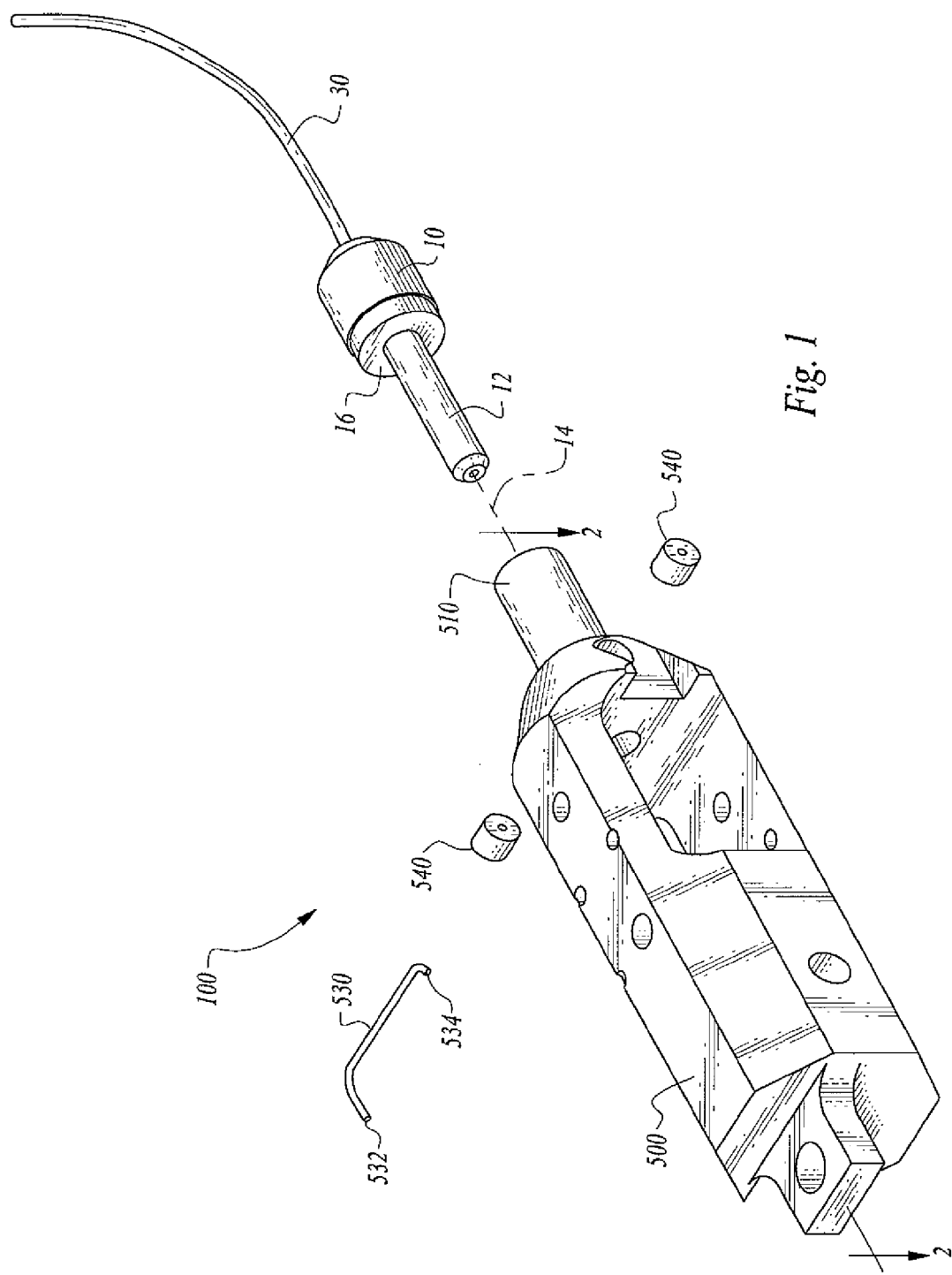
FIG. 1 is an exploded perspective view of an embodiment of disposable tip apparatus 100 with alignment assembly adapted to a reusable surgical device laser housing 500.

With reference to drawing FIGS. 1-3, disposable tip apparatus 100 and 100A for optical alignment with reusable laser surgical device are presented. The reference numerals 100 and 100A designate generally typical apparatus for optical alignment of a disposable tip with a reusable laser surgical device.

Our disposable surgical tip apparatus disclosed and claimed in the '336 Application is incorporated herein by reference for all purposes.

An embodiment for apparatus 100 for optical alignment of a disposable tip with a reusable laser surgical device, includes the following combined elements: a disposable tip housing 10 with a first end 12 having a longitudinal axis 14 and adapted to releasably fit on the distal end 510 of the surgical device laser housing 500; optical fiber means 30 for delivery of light energy axially positioned within the tip housing 10 from within the first end 14 and extending beyond the housing 10; assembly 16 for releasably locking the tip housing first end 14 to the surgical device laser housing assembly 500; and assembly for aligning optical fiber means 30 within the tip housing 10 to a source of laser light energy, such as a diode laser, within the surgical device laser housing assembly 500 for surgical laser treatment.

The tip apparatus 100 provides a channel 520 within the surgical device laser housing assembly 500 sized to receive the tip housing first end 12 along the longitudinal axis 14 for aligning the optical fiber means 30 within the tip housing 10 to the surgical device laser housing assembly 500. The surgical device laser housing assembly 500 is adaptably sized and configured to direct diode laser light energy from within the laser housing assembly 500 to the optical fiber means 30 within the tip housing 10 once the tip housing first end 12 is fully positioned within the surgical device channel 520.

An embodiment of the tip apparatus 100 provides a conductive wire sensor 530 made from gold plated steel and having two ends, 532 and 534, within the surgical device laser housing assembly 500 positioned transverse to the tip housing longitudinal axis 14, whereby the conductive wire sensor 530 contacts the tip housing first end 12 when it is fully positioned within the surgical device channel 520. Contact between the conductive wire sensor 530 and tip housing first end 12 causes the conductive wire sensor 530 to close an electrical circuit (not shown) within the surgical device laser housing assembly 500 and allows use of the tip apparatus 100, FIGS. 1 and 2.

The conductive wire sensor 530 is housed within the surgical device housing assembly 500 by insulated tubing 540.

An embodiment of the apparatus 100 provides an assembly 16 for releasably locking the first end 12 to the laser housing channel 520 comprising at least one member of the group consisting of means for magnetic coupling, means for mechanical coupling, means for electromechanical coupling, and means for electromagnetic coupling.

A second embodiment 100A includes an emitter element 50 and a detector element 52 providing an optical sensing assembly, FIG. 3, to indicate when the tip housing first end 12 is fully positioned within the surgical device channel 520 and properly aligned with the laser housing assembly 500. When the tip housing first end 12 is properly positioned within the surgical device channel 520 and properly aligned with the laser housing assembly 500, the optical sensing assembly closes an electrical circuit (not shown) within the surgical device laser housing assembly 500 and allows use of the tip apparatus 100A.

An embodiment of the tip housing 10 is made of at least one member of the group consisting of polyimide, polycarbon, stainless steel, steel, iron, plastic, and aluminum.

An embodiment of the tip apparatus 100 is packaged as a sterile assembly.

It should be understood, of course, that the specific forms of the invention illustrated herein and described are intended to be representative only, as certain changes may be made therein without departing from the clear teachings of the disclosure. Accordingly, reference should be made to the following appended claims in determining the full scope of the invention.

We claim:

1. A tip apparatus for a reusable laser surgical device, the tip apparatus comprising:
   a) a disposable tip housing with a first end having a longitudinal axis and adapted to releasably fit on the distal end of the surgical device;
   b) an optical fiber for delivery of light energy axially positioned within the tip housing and extending beyond the tip housing;
   c) means for releasably locking the tip housing first end to the surgical device; and
   d) a laser housing assembly that receives the first end of the tip housing, wherein the laser housing assembly includes a channel that is sized to receive the tip housing first end along the longitudinal axis, and a conductive wire sensor having two ends positioned transverse to the tip housing longitudinal axis, whereby the conductive wire sensor contacts the tip housing first end when it is properly positioned within the channel, and wherein contact between the conductive wire sensor and the tip housing first end closes an electrical circuit.

2. The tip apparatus of claim 1, wherein the conductive wire sensor is housed within the laser housing assembly by insulated tubing.

3. The tip apparatus of claim 1, wherein the wire sensor comprises gold plated steel.

4. The tip apparatus of claim 1, wherein the laser housing assembly includes an emitter element and a detector element positioned on either side of the channel, whereby the emitter and detector elements can detect whether the tip housing first end is positioned in the channel.

5. The tip apparatus of claim 1, wherein the means for releasably locking the first end to the surgical device comprises at least one member of the group consisting of means for magnetic coupling, means for mechanical coupling, means for electro-mechanical coupling, and means for electro-magnetic coupling.

6. The tip apparatus of claim 1, wherein the tip housing is made of at least one member of the group consisting of polyimide, polycarbon, stainless steel, steel, iron, plastic, and aluminum.

7. The tip apparatus of claim 1 packaged as a sterile assembly.

* * * * *